(12) United States Patent
Smith

(10) Patent No.: US 11,395,764 B1
(45) Date of Patent: Jul. 26, 2022

(54) EYE IMPLANT DEVICES AND METHOD AND DEVICE FOR IMPLANTING SUCH DEVICES FOR TREATMENT OF GLAUCOMA

(71) Applicant: S. Gregory Smith, Wilmington, DE (US)

(72) Inventor: S. Gregory Smith, Wilmington, DE (US)

( * ) Notice: Subject to any disclaimer, the term of this patent is extended or adjusted under 35 U.S.C. 154(b) by 150 days.

(21) Appl. No.: 16/250,076

(22) Filed: Jan. 17, 2019

Related U.S. Application Data

(63) Continuation-in-part of application No. 11/292,975, filed on Dec. 3, 2005, now abandoned, and a continuation of application No. 14/175,572, filed on Feb. 7, 2014, now Pat. No. 10,219,942.

(51) Int. Cl.
*A61F 9/007* (2006.01)

(52) U.S. Cl.
CPC ................. *A61F 9/00781* (2013.01)

(58) Field of Classification Search
CPC .. A61F 9/00781; A61F 9/0017; A61F 9/0133; A61F 2009/00865; A61F 2009/00891
See application file for complete search history.

(56) References Cited

U.S. PATENT DOCUMENTS

| RE35,390 E | * | 12/1996 | Smith | ................. A61F 9/00781 604/8 |
| 2002/0165478 A1 | * | 11/2002 | Gharib | ............... A61F 9/00781 604/8 |

OTHER PUBLICATIONS

Alward, W. L. "Biomedicine: Enhanced: A New Angle on Ocular Development." Science, vol. 299, No. 5612, 2003, pp. 1527-1528.*
Andres-Guerrero, Vanessa et al. "Targeting Schlemm's Canal in the Medical Therapy of Glaucoma: Current and Future Considerations." Advances in therapy vol. 34,5 (2017): 1049-1069.*

* cited by examiner

*Primary Examiner* — Thomas McEvoy
(74) *Attorney, Agent, or Firm* — Andrew L. Salvatore, Esquire

(57) ABSTRACT

The present invention provides for a deformable, insertable device for relieving intraocular pressure comprising a body portion composed of a biocompatible porous material with pores throughout to permit drainage of fluid from the anterior chamber to the scleral tissue without collapse of the anterior chamber. The invention also includes a method for inserting the device into the eye and for using ultrasound intraoperatively to determine the position of surgical tools and devices within the sclera. The invention also includes a device excising sclera in an eye to create a chamber for insertion of the insertable device into the eye.

1 Claim, 7 Drawing Sheets

EYE IMPLANT DEVICES AND METHOD AND DEVICE FOR IMPLANTING SUCH DEVICES FOR TREATMENT OF GLAUCOMA

CROSS REFERENCE TO RELATED APPLICATIONS

This application is a continuation in part application of, and claims priority to, U.S. patent application Ser. No. 11/292,975 filed on Dec. 3, 2005 and is a continuation of, and claims priority to U.S. patent application Ser. No. 14/175,572 filed on Feb. 7, 2014. The above referenced prior applications are hereby incorporated herein by reference.

BACKGROUND OF THE INVENTION

This invention relates to the drainage of aqueous humor from eyes in the course of relieving eye disorders. Specifically, the invention relates to an implant which, when permanently affixed to or implanted in a specific area of the eye, will provide such drainage efficiently, for longer periods than heretofore accomplished, and, in short, will provide relief and prevent, or at least postpone, the adverse ultimate effects of glaucoma. The present invention also relates to a method for inserting the implant, and a surgical device for inserting the implant.

The eyeball is composed of three basic layers: (1) the sclera; (2) the middle layer or choroid; and (3) the retina. The sclera 10 is the outer layer of the eyeball. It consists of tough, white tissue that serves as the supporting framework of the eye. At the front of the eye, the sclera is continuous with the clear, transparent cornea 20 through which light enters the eye. The clarity of the cornea is maintained by the delicate layer of cells on the posterior side thereof, called the endothelium 30. If a foreign material, such as plastic, metal, hydrogen, silicon, etc., touches the endothelium, these cells will die. However, because of the nature of the endothelium cells, which are designed to pump fluid out of the cornea, the death of these cells can impair the vision of the eye. The corneal endothelial cells have tight junctions between them so that fluid will not leak into the cornea and thus need to be pumped out. Should an endothelial cell die, the adjacent cells will expand their size and grow together to reform the tight junction to effect a seal. When such a cell dies, other endothelial cells will migrate and expand into the area previously occupied by the dead cell. A device or other foreign object placed into the trabecular meshwork area of the anterior chamber of the eye should be less than 20 microns in external diameter to avoid touching the corneal endothelium. If the device touches the endothelium, progressive endothelial cell loss will occur, causing the cornea to cloud, causing loss of vision and ultimately for the need for a corneal transplantation. Behind the cornea is a small space, the anterior chamber, which contains a clear watery fluid called the aqueous humor.

The middle layer is composed of three parts: (1) the choroids; (2) the ciliary muscle 310; and (3) the iris 40. The choroid lies behind and to the sides of the eyeball making up about 80% of the middle layer. It contains most of the blood vessels that nourish the eye.

Toward the front of the eyeball, the choroid becomes the ciliary muscle 310. This muscle is connected by fibers to the lens 50, keeping the lens in place and controlling its shape. At the very front, the middle layer becomes the iris, a thin curtain of tissue in front of the lens. A round opening in the iris, whose size is controlled by muscles in the iris, is called the pupil 60.

In simple terms, the cornea refracts light through the anterior chamber 70 and then through the pupil, the entrance aperture of the eye to the lens. The lens serves to focus the refracted light through the vitreous chamber 80 containing the vitreous humor onto the retina, the rear surface of the eye.

As shown in FIGS. 1-3, normally the fluid within the eye, the aqueous humor, is produced by the ciliary body 90 and migrates through the pupil into the anterior chamber, the small space behind the cornea. From this chamber, the liquid migrates through the trabecular meshwork 100 through Schlemm's canal 115 and into the aqueous veins which form fluid collection channels beneath the conjunctiva 150, the latter covering the front of the eyeball except for the cornea.

When the aqueous, migration, described above, is insufficient to relieve the build-up of intra-ocular pressure, glaucoma results. This pressure build-up is usually thought to be due to one or more obstructions in the trabecular meshwork through drainage areas behind the trabecular meshwork which can also impede flow of fluid out of the eye. Unless controlled, the high pressures associated with glaucoma ultimately leads to permanent damage of the optic nerve, the nerve formed from the sensitive fibers of the retina.

The prior art shows many implantable devices and methods of implanting them, but the majority violate the wall of the sclera adjacent to the vascular tissue of the conjunctiva. Such violation causes stimulation of vascular tissue. The majority of the prior art also discloses methods and devices that violate the corneal endothelium.

The prior art disclosed an approach to avoid the problem of fluid pressure buildup that involved implanting a device in the sclera. It was noted in surgical studies that the intraocular pressure would drop significantly with the use of this type of device but that over time some eyes would have a rise in intraocular pressure corresponding to a clinical trapping of the aqueous fluid around the implant in the sclera. The sclera is a non-reactive tissue; it only heals when vascular tissue from above or below grows into it. The sclera is also composed of a meshwork of fibrous tissue with passageways or spaces as large as 150 microns. The present invention provides an improved insertable device and a method of inserting such a device into the sclera without causing the conjunctiva to heal and thus block the fluid egress created by the device.

The object of the present invention is to provide a device that can be implanted permanently, simply and effectively to permit substantially normal migration of fluid out of the anterior chamber of the eye and, thus, avoid the abnormal build-up of intra-ocular pressure. Another object is to provide the implant in a manner that will also avoid excessive migration of fluid that would lead to collapse of the anterior chamber with its accompanying complications.

Another object of the present invention is to provide a device and method of implanting the device that eliminates the problem of healing of the conjunctiva and tenon's tissue. Another object of the invention is to provide an implant or insertable device and a method of inserting the implant or device that prevents it from contacting the corneal endothelium. Finally, another object of the invention is to provide a device that is deformable and recoverable to allow it to pass through multiple incisions.

SUMMARY OF THE INVENTION

The present invention provides a method for inserting an intraocular pressure relieving device into an eye comprising cornea, a lens, sclera, conjunctiva, and corneal endothelium; Determining a site for locating the pressure relieving device; Making a corneal incision in an area remote from the site for locating the pressure relieving device; Inserting a drill or laser, or radiofrequency, cautery, or mechanical tool into the corneal incision; Creating an opening or passage with the drill or laser or above mentioned devices; Extending the opening or passage into the sclera of the eye remote from the corneal incision; Forming a chamber or pocket at a terminal end of the opening or passage in the sclera of the eye; Removing excess sclera from the chamber or pocket; Deforming a pressure relieving device 120; Inserting the deformed pressure relieving device through the opening/passage and into the chamber or pocket; Allowing the deformed pressure relieving device to return to its original form once it is placed in the chamber or pocket.

The present invention provides a method of relieving intraocular pressure in an eye, the eye comprising a cornea, conjunctiva, tenons, vascular tissue and sclera, the method consisting of inserting a glaucoma drainage device without making an incision in the conjunctiva or tenons.

The present invention provides a device 200 for excising sclera in an eye to form a chamber for insertion of a device for relieving intraocular pressure comprising: A blade carrying body 220; At least one moveable cutting blade 210 having a first or retracted position and a second or extended position wherein at least one cutting blade extends beyond the body; Means for moving 230 the cutting blade from the first position to the second position, and back to the first position; Means for moving the at least one cutting blade, while in the second position, around the body.

The device may contain a means for moving the cutting blade from the first position to the second position which comprises a cam shaft and a cam cut. The blade may also be moved by means of a chain, pulley, gear and cog. The device may also contain a means for vibrating the cutting blade such as a motor inserted within the device or an ultrasonic device. The device may also contain more than one cutting blade. The blades may contain a cutting tip at a distal end of each blade, and the cutting tip may be bent from the bent from the plane of the cutting blade. The cutting tip may be bent from 60° to 90° from the plane of the cutting blade.

The present invention provides a deformable implantable pressure relieving device for the treatment of glaucoma which, once deformed, returns substantially to its original shape. The devices of the present invention can be comprised of pores, passageways, channels, or tubes. They can also be present on the surface of the device.

The present invention provides a method for creating chambers consisting of: creating a passageway; inserting a device with guarded blade or blades; retracting the guard; applying power to the blades so that they expand and cut material to a size larger than the entry passageway; Redeploying the guard over the blade or blades; Removing the device through the original passageway.

The present invention also provides an implantable device 120 for relieving aqueous pressure in an eye comprising a system of passageways, pores, or channels formed through the device and on its surface.

The present invention also provides a method of inserting a deformable pressure relieving device 120 into an eye comprising; deforming the device; inserting the device into a delivery device; creating a passageway in the eye; creating a chamber at a terminal end of the passageway; inserting the delivery device through the passageway and into the chamber; ejecting the pressure relieving device from the delivery device and into the chamber.

DETAILED DESCRIPTION OF THE INVENTION

Figure 1:
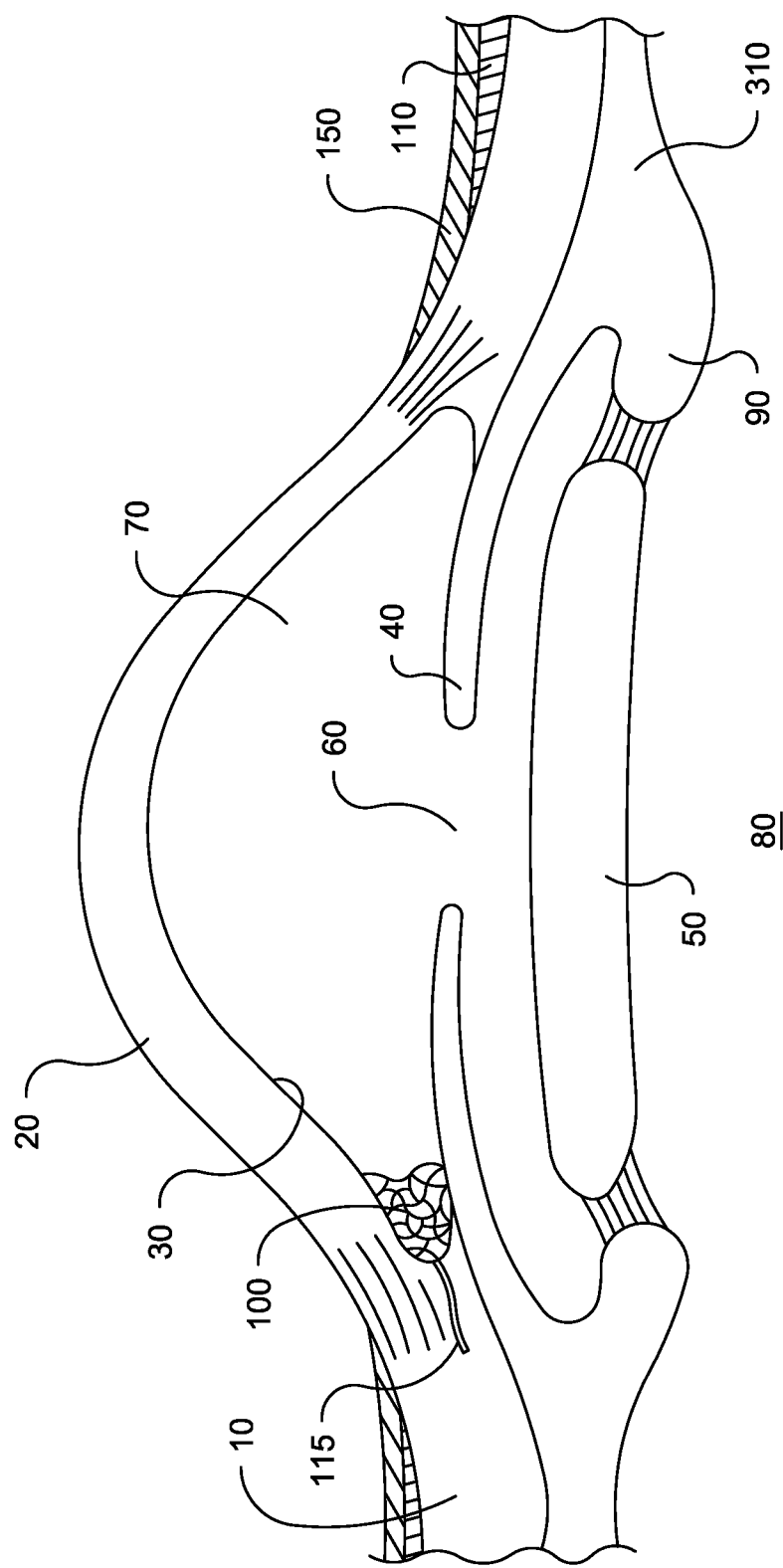
FIG. 1 shows a cross sectional view of an eye.
Figure 2:
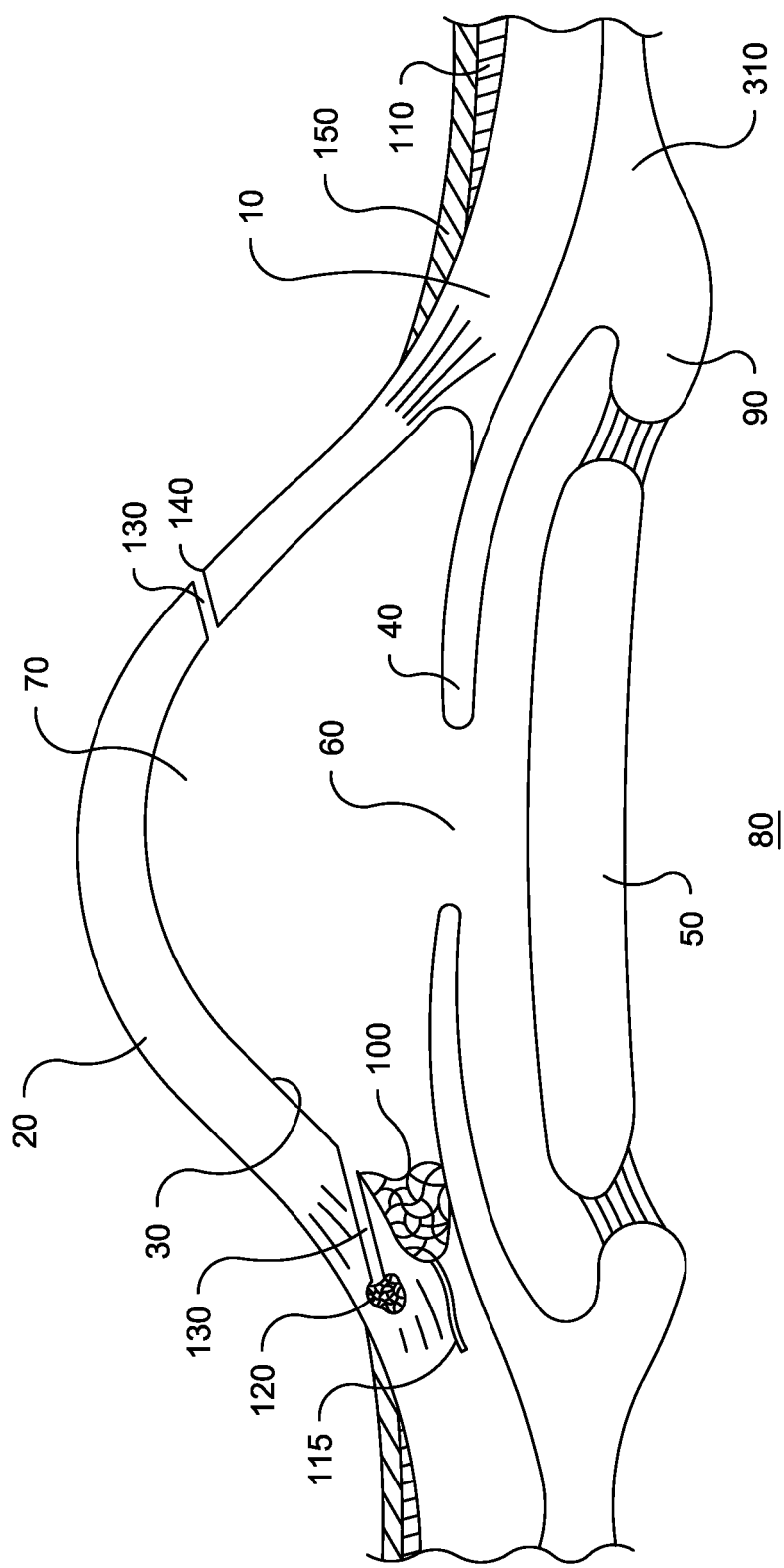
FIG. 2 shows a cross sectional view of an eye with implantable device according to the invention and path of incision.
Figure 3:
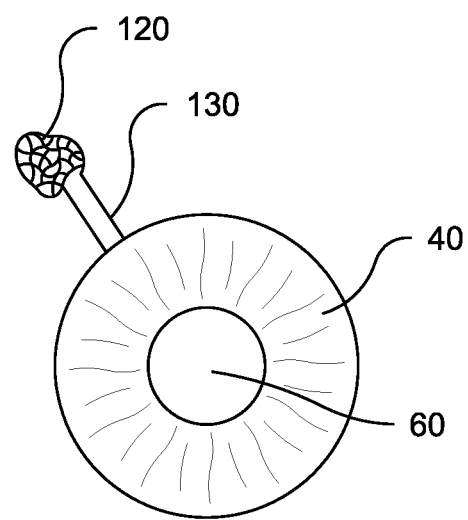
FIG. 3 shows a front elevational view of an eye with implantable device according to the invention and path of incision.
Figure 4:
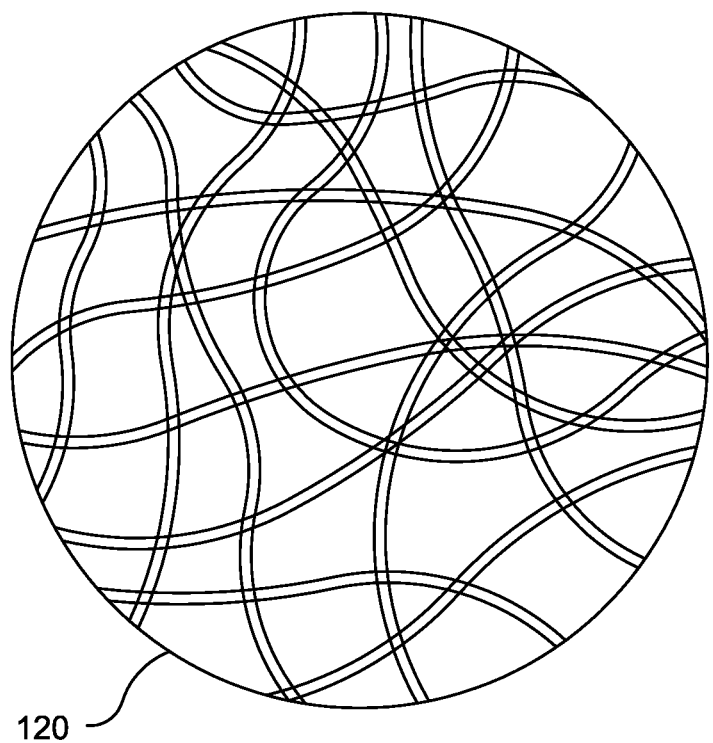
FIG. 4 shows a front elevational view of an implantable device according to the invention.
Figure 5:
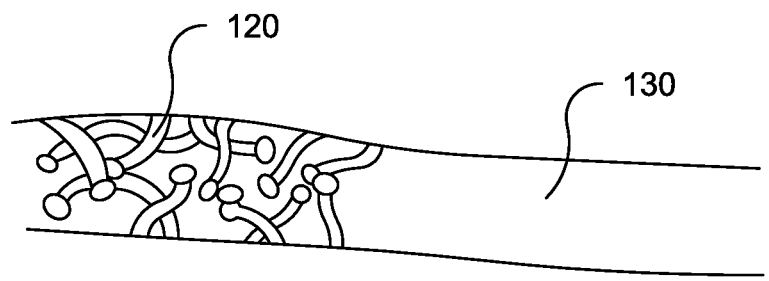
FIG. 5 shows a side elevational view of an embodiment of an implantable device according to the invention.
Figure 6:
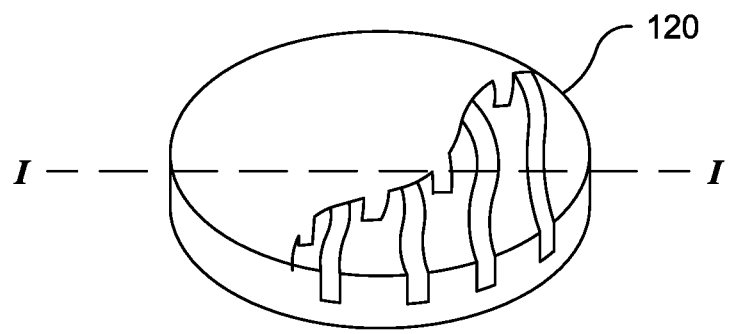
FIG. 6 shows a partially cut away perspective view of an embodiment of an implantable device according to the invention.
Figure 7:
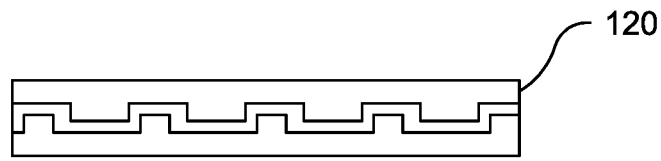
FIG. 7 shows a cross sectional view of an embodiment of an implantable device taken at line I in FIG. 6 according to the invention.

The present invention provides a device and a method for reducing intraocular pressure that is free of the problems associated with prior devices and methods. The description below illustrates possible embodiments of the present invention and are in no way meant to be limiting. Other embodiments within the scope of the invention will be clear to those skilled in the art.

The improvement of the present invention is in the device, the method, and the instrumentation for the technique of surgery. The surgery for reducing intraocular pressure typically involved inserting a device into the eye, such device facilitating the flow of aqueous humor from the eye. The insertable device can be made of a biocompatible material that is foldable and the returns to its original shape. The insertable pressure relieving device 120 can comprise a system of channels, pores or passageways on the surface and/or through the device, to allow for the flow and drainage of aqueous humor and thus prevent pressure build up. The deformability of the device allows it to be implanted through a small incision 130. FIGS. 4-7 and 9 depict various embodiments of the device which allow fluid to pass through the device or across its surface.

The opening should be in the area or near the area at which the trabecular meshwork exists in an area which allows the best access to the sclera. According to the methods of the present invention, the insertion surgery can now be performed in a completely novel way. Instead of a large 8 mm or greater incision into the conjunctival tissue and further incisions into the sclera which would allow the ingrowths of vascular tissue (such tissue would seal off the openings in the sclera wall and block the egress of fluid through the sclera and therefore raise the intraocular pressure "IOP") and incision 130 is made into the nonvascular cornea at a remote location 140 and entry into the sclera is made from the anterior chamber. Thus, the conjunctiva is not incised and the wall of the sclera is not opened (in a preferred embodiment of the method of the present invention).

According to the method of the present invention, the healing response of the conjunctiva and tenon's tissue 110 is not stimulated because there is no incision in these tissues and no fibrovascular growth can access into the sclera since there is no incision in the sclera in an area where vascular tissue exists. Such ingrowths of vascular tissue would cancel the effects of the pressure relieving device, causing the device to fail by blocking the channels or pores with vascular tissue.

The insertable pressure relieving devices 120 of the present invention can be made in a wide variety of shapes, such as rectangular, square, cube or triangular polyhedrons, pyramids, orbs spheres, etc. These shapes can be two or three dimensional, preferably three dimensional, and having a depth of approximately 0.2 mm. The shape of the device should be such that it will fill the pocket or chamber of tissue removed from the wall of the sclera and therefore resist migrating back through the small incision through which it was implanted. The present invention provides for a device which is compressible or foldable so that it can go through a small incision and expand back to it's initial shape, a means for inserting such a device, and for creating a pocket where such a device can be implanted. The pocket created according to the present invention is larger in dimension than the small incision through which the pocket is accessed, and through which the implant is inserted.

The implantable device can be made from a wide variety of materials, preferably those that are biocompatible. Biocompatible materials that can be used include hydrogels, silicons, acrylics, hydrocarbons, and polymethylmethacrylate, a polyurethane elastomer, a silicone elastomer, a hydrogel polymer, a collagen compound, a collamer, an organic gel compound, and a synthetic gel compound. Preferably, the biocompatible material or combinations of materials can also be deformed, and once deformed will return to substantially their original shape.

A distinct advantage of this surgery compared to traditional glaucoma surgery is that it can be performed with topical anesthesia. The patient is brought in to the operating room and the eye is anesthetized with topical lidocaine or equivalent. The operating microscope is brought into view and the site for the implant is determined. A stab incision into the cornea is made roughly 180 degrees from the selected site. Unpreserved lidocaine 1% is irrigated into the anterior chamber. A gonio lens of the Koeppe type is place on the cornea. This allows the surgeon to view the anterior chamber angle through the operating microscope. Once this view of the trabecular meshwork is obtained a viscoelastic component such as hyaluronic acid Amvisc® is injected into the anterior chamber to push the iris back and protect the cornea. A drill is then placed through the stab incision and then introduced across the anterior chamber to the trabecular meshwork area. This drill is approximately 0.2 mm in diameter. It can extend to a diameter of 0.6 mm as the sclera ranges from 0.7 mm to 1 mm thick in normal eyes. The drill is then used to enter the wall of the sclera. Care is taken to direct the drill into the wall of the sclera and not above or below the sclera for this most ideal form of surgery. The operating microscope can be used to obtain a direct view of this area using the Koeppe lens or equivalent. The drill is then used to make a passageway 2.25 to 2.50 mm within the sclera. This distance can be controlled by a stop on the body of the drill bit. Once this is completed the drill is withdrawn and further viscoelastic material is placed in the angle of the anterior chamber Where the iris and cornea come together, (this is where the sclera begins) to move the remnants from the area.

Figure 8:
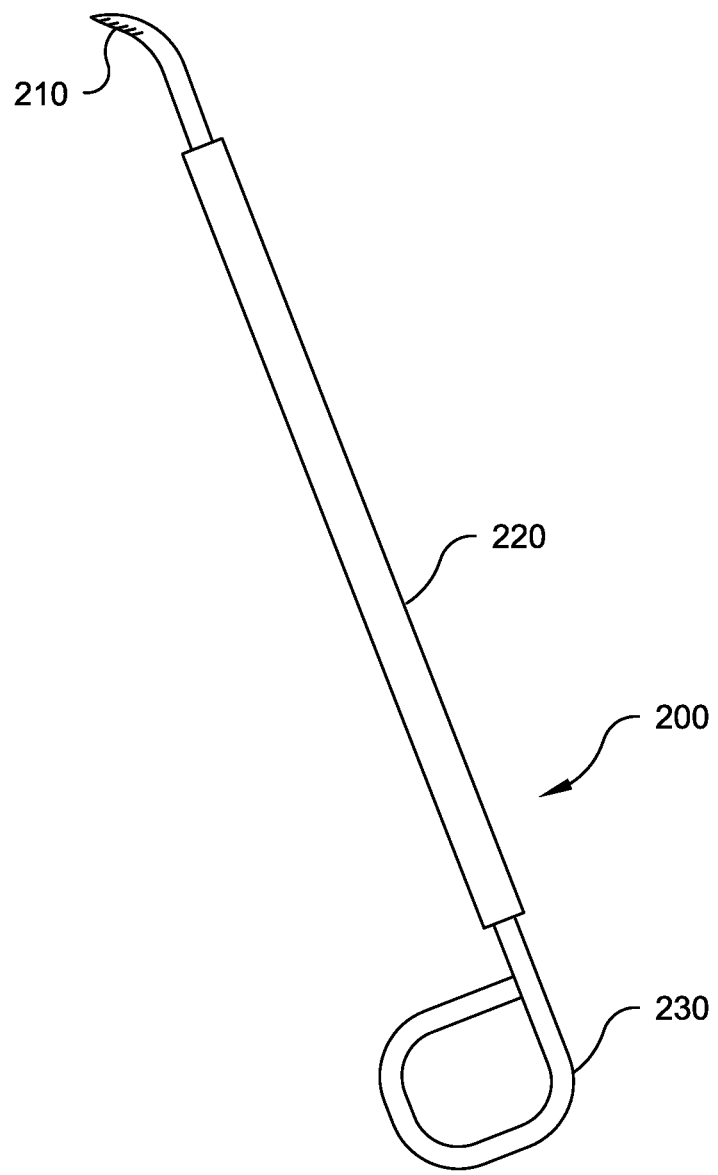
FIG. 8 shows a top plan view of a pocketmaker device for excising sclera according to the invention.
Figure 9:
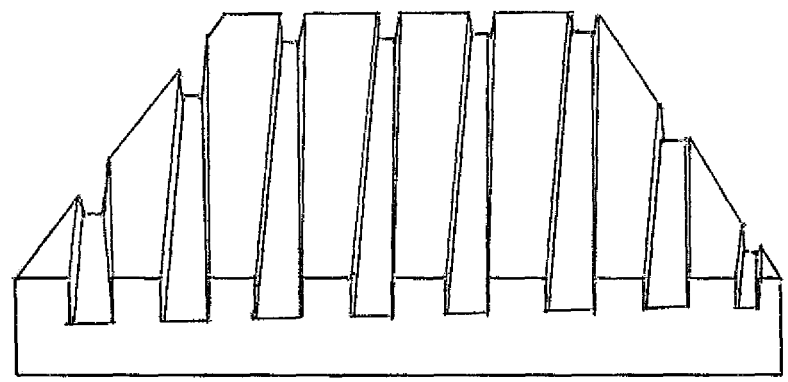
FIG. 9 shows a perspective view of an embodiment of an implantable device according to the invention.

A second instrument of the present invention, as shown in FIG. 8, a pocketmaker device 200 for excising sclera in an eye can then be placed through the stab incision, across the anterior chamber, and into the hole made by the drill. Various embodiments of the pocketmaker device of the present invention can include at least one means for cutting. In the preferred embodiment the pocketmaker would consist of a small disc with two blades which were freely movable. The disc would be attached to a drive train consisting of various gears to transfer the force from the shaft to the disc itself. These types of gears are well known in the art such as automobile transfer of energy to the wheels. The disc with cutting assembly folded would insert through the corneal incision, across the anterior chamber and into the hole drilled in the sclera in the area of trabecular meshwork. The drive shaft would be approximately 15 mm long with a diameter of approximately 0.2 mm, a protective sleeve could slide over the blade carrying body containing the two folded blades. The drive shaft could be much longer if chosen, however, it needs to be long enough to extend across the anterior chamber and into the drilled opening.

Once the disc is guided into the opening previously drilled the protective sleeve could then be retracted. For example, the sleeve, or a portion or attachment to the sleeve, could extend outside the corneal incision with a small protrusion on it to allow the surgeon to manually pull it back. This would then expose the twin blades which when fully extended would create a diameter of 3 mm. (In this situation a 3 mm round implant approximately 0.2 mm in diameter would be used.) Once power is applied to the drive train and therefore causes the disc to rotate at high speeds a round opening in the sclera approximately 3 mm in diameter would start to be created opposite the drilled incision. With proper preset angulation of the blades, movement upwards would create a pocket with a depth of 0.2 mm.

The use of real time ultrasonography on the sclera above the area of surgery would be of great help in determining the exact thickness of tissue being removed. It would also be helpful to use during the drilling maneuver performed earlier to achieve the optimum location.

A further improvement would be the use of irrigation and aspiration around the drive train. The initial diameter may need to be larger in this embodiment as the shaft would contain a hollow tube internally to which suction is supplied from a peristaltic pump or venturi pump and an outer sleeve which contained irrigating fluid supplied by the force of gravity (for example, by hanging a bottle of irrigating fluid and attaching it to this handpiece.) In this manner the excised pieces of sclera can be removed while the surgery is taking place by irrigating fluid into the newly created chamber and aspirating these pieces and the fluid. This may also provide cooling to the instrument and the tissue.

Once the pocket has been created the sleeve and be pushed back onto the disc and over the blades. This would push the blades in the opposite direction than they were initially loaded in but will prevent the blades from cutting tissue as the pocket maker is removed.

The prior art has described multiple ways of folding intraocular lens implants and delivering them into the eye. The glaucoma device would be folded in a similar manner into an injector, for example, one that uses a screw type delivery system that pushes the device out through a small tube. Unlike the intraocular lens implanters, this inserter would require the use of an extended delivery tube of approximately 14 mm minimum inside the eye with the standard working distance outside the eye. (Current devices extend a maximum of 6 to 8 mm inside the eye.) Viscoelastic material would then be placed into the anterior chamber, via an injector, which would be placed through the corneal incision, across the anterior chamber, and into the sclera tunnel which had been drilled. By twisting the screw mechanism of the delivery system, the plunger would extend through the tube delivering the glaucoma implant into the pocket created. The deformable implant would then expand to its original shape, filling the chamber or pocket created for it. The inserter would then be retracted out of the tunnel and then the eye. The deformable implant would be trapped in this chamber or pocket, as it is bigger than the scleral tunnel leading from the pocket or chamber. A plunger type of inserter could also be used.

The use of a light pipe with visualization capability could be used to confirm location in addition to using ultrasonagraphy, as mentioned previously.

In a second embodiment, the pocketmaker can comprise two retractable blades attached to linear body for example, two wheels or pulley s attached linearly. These blades can be moveably attached to the body of the pocket maker. The movement of the blades can be by direct drive or chain means, or any other means for moving the blades around the body of the pocketmaker device. This pocketmaker device can also comprise means for extending the blades and means for retracting the blades. The pocketmaker device is preferably inserted into the incision discussed above with the blades in the retracted position. Once inserted into the end of the passageway, the device can be activated so that the blades are moved into the extending position. Once in the extended position, the blades can be driven around the body of the pocketmaker device, cutting an area larger than the passageway through which the device was inserted, and creating a chamber at the end of the passageway.

The twin blades of the pocket maker are then deployed by backing up (pushing the trigger forward) on the trigger. The twin blades are then advanced by repeated squeezing of the trigger (for this embodiment). This drives the blades forward, then around, then back, then up, then forward again. This results in a block of sclera 2 by 3 mm being excised. The blade on the right and the blade on the left each excise a quadrilateral 3D structure 1.4 mm by 1 mm. (the drill has already removed a piece that is 0.2 mm in diameter.) In alternate embodiments, the tip of each blade can be bent, preferably at about a 90 degree angle, but lesser angles can also be used, so that when the blades are driven around the body of the pocketmaker, a complete dissection of the surrounding tissue has been completed. The angle of the tip of the blade can depend on the size of the chamber or pocket to be formed. The size of the blades can be altered to adjust the amount removed. It would be expected that the blades could be easily replaced on the pocket maker. The pocket maker can be withdrawn by inserting a sleeve that urges the blades back into the retracted position.

Once the device has been removed, a long forceps with small teeth such as a Utrata is introduced into the anterior chamber, across the iris, and into the drill hole. One half of the cut sclera is grasped with the forceps and removed. The second half is then removed in similar fashion.

The deformable implant is then placed into a folder and compressed and deformed so that it fits through the 0.2 mm incision. The folder is autoclaveable. The folder is then inserted into the anterior chamber and directed to the previously made drill hole of 0.2 mm with the pocket of 2 mm by 3 mm behind it. There is approximately 0.5 mm of sclera remaining between the anterior chamber and the pocket. For this embodiment, we will assume it is a screw type delivery mechanism to deliver the device. The device is simply delivered into the pocket previously made and it returns to its original shape it had prior to being deformed. It is now, however, trapped in the scleral pocket.

Other methods for making the tunnel or bed could be employed. The tunnel could be made with a laser on the end of a tube. YAG lasers, and excimer lasers, for example, have this capability. A radiofrequency or ultrasound driven tip such as those used in phacoemulsification could also be used. There are numerous manufacturers of these types of ultrasonic handpieces currently know in the field. By lengthening the tip of these preexisting handpieces the device would be able to reach across the anterior chamber and be able to extend into the sclera. The ultrasonic handpiece could then be used to make both the initial tunnel and then by directing the tip on a slight angle to both sides it could create a pocket greater in at least one dimension than the opening. After irrigating and aspirating the scleral remnants the implant could be folded and inserted into this pocket.

Using the first incision into the sclera, a tunnel (preferably roughly 0.3 mm in size) would be made. Techniques for making the tunnel can include drilling, emulsifying, lasering, grinding, cutting, or using instruments capable of taking bits of tissue. This tunnel would be made to the point of eventual implantation of the device.

There currently exist 20 gauge instruments which contain a light pipe and a video system. Such a device would be placed through the corneal incision and into the sclera incision.

Using a two handed technique, the light pipe and video in one hand, and a cutting instrument in the other hand, a scleral pocket could be created in a fan shaped pattern. The cutting instruments would be those discussed above for making the initial scleral tunnel. For example if an emulsifying unit was used, an initial pass creating a tunnel could be made. The light pipe video viewing system could be inserted here. Through a second stab incision in the cornea a second tunnel could be made on such an angle that the two intersect. Then, using the video system scleral tissue could be removed in a fan shape with the point of the fan being the second entry site. Visualization would be obtained through the video system of where tissue was being removed. When the process was completed a triangular bed of tissue would have been removed with two access ports into it, the one at the apex and the one for the video unit. An implant designed to fit this type of space, triangular in shape with appropriate thickness (i.e. that of the emulsifying unit) could be inserted.

The emulsifying unit could employ irrigation and aspiration as described previously for the same reasons. The other instruments, lasers, drills, blades, grinders, instruments to take bites of tissue could all be used to perform this. Irrigation and aspiration could be combined with these as well.

Once the incision or passageway has been created to the depth of the desired position of the implantable device, a device of the present invention can be used to create a pocket or chamber for the insertion of the implantable device. The creation of this pocket or chamber can be accomplished by the method of the present invention, as well as by the use of a device of the present invention. A device of the present invention for creation of the pocket or chamber can be called a pocketmaker device. This device accomplishes a step in the method of the present invention, namely, creating a pocket or chamber. The device comprises a body and at least one blade, preferably two blades. The blades are moveably mounted on the body and can be controlled by an individual. Such control can be manual, by the use of small chains, pulleys, conveyors and similar devices connected to the device. The device can also comprise a means for extending and retracting the blades. The blades should be retracted so that the pocketmaker device can be inserted through the small incision, and then extended so that the device can be used to create a pocket of larger dimension than the small incision through which the device was inserted. The blades can be extended manually by manipulation of the chains, pulleys or conveyors, or by automated motor controlled externally by radio or other electronic means. Such remote control means are known in the art, as are such manual means of activating and controlling the blades. In addition, the blades can be spring loaded and urged into the extended position. The pocketmaker device can be inserted into an injector or sleeve that presses the blades into the retracted position. Once the pocketmaker is inserted into position and ejected from the injector or sleeve, the blades will move to the extended position. After the pocketmaker had created a pocket or chamber, the sleeve can be reinserted into the incision, and pressed over the pocketmaker, urging the blades into the retracted position and allowing the pocketmaker to be removed.

The pocketmaker device can further comprise a drive means for moving the blades around the body of the device. Such drive means can comprise a system of chains or pulleys, a track with teeth, gears and cogs, or other means, all attached to a motor or driving means, of propelling the blades around the body of the pocketmaker device. The drive means should be capable of driving the blades around the body of the pocketmaker device. In addition to drive means, the pocketmaker device can further comprise means for vibrating the blades, so that the blades can cut through the scleral tissue more efficiently as the blades are driven around the body of the pocketmaker device.

In embodiments of the present invention, the blades can further comprise an angled cutting tip and each end thereof. The tip should be located at the end of the blade farthest from the body, and preferably comprise a 90° bend whereby the blades, when driven or rotated about the body of the pocketmaker device, can create a pocket or chamber shaped cut. Once the cut tissue is removed, the extended and driven blades will have created a chamber that is larger than the initial incision through which the pocketmaker was inserted. The larger dimensions of this chamber or pocket are useful in inserting a pressure relieving device, so that once the pressure relieving device has been inserted into the chamber or pocket, it cannot easily migrate out or change position.

Once an area has been removed, for example creating an intrascleral space approximately 0.2 mm in height, roughly triangular or a rectangle or quadrilateral shape (by switching instruments insertions) the device could then be implanted.

The implantable device would be folded, placed in an inserter, introduced through the incisions in the cornea, into the opening in the sclera, and then injected. It would expand back to its original form, filling the space made, fluid would access through the opening into the anterior chamber, no sutures would be necessary and the conjunctiva is disturbed for a miniscule amount at a site remote from the device.

In this manner, no incision is made in vascular tissue. The cornea has no vessels. The sclera has an occasional vessel which goes through it. The sclera heals only by secondary intention. Since the conjunctiva and tenons tissue have not been violated no blood vessels will grow in from above. Since the ciliary body has not been violated from below, no blood vessels will grow in from this source. There are no blood vessels in the anterior chamber for the normal eye and all glaucomas except for neovascular glaucoma. The intrascleral deformable device would not be indicated in neovascular glaucoma as the progressive growth of scar tissue (called peripheral anterior synechiae) will close over the sclerostomy (the opening made by the drill into the anterior chamber). A further advantage of this surgery is that the corneal endothelium is never in contact with the implant. The implant is recessed behind the opening (sclerostomy).

The implantable pressure relieving devices of the present invention should be sized to fit the space created by the pocketmaker, but can be made in a wide variety of sizes and shapes. For example, if the chamber or pocket created is a circle 3 mm in diameter and has a depth of 0.2 mm, the implantable device should be manufactured to fit this space. The implantable device should be deformable and can comprise a system of passageways, pores, or channels through it and/or on its surface. Fluid accessing the device would then be distributed throughout the sclera of the eye.

The pressure relieving devices of the present invention can be deformed, preferably folded, by a wide variety of devices or methods. For example, the implantable pressure relieving device can be placed in a cartridge, pushing down on the middle of the implant and then folding the cartridge together so the device is now folded in half. The cartridge and deformed pressure relieving device can be placed in a screw delivery device. By turning the screw a plunger gradually pushes the device out of the cartridge through a constricting end which further compresses the device to the size desired, preferably 0.2 to 0.3 mm. However, the size and shape desired will depend on the shape and size of the pocket or chamber formed according to the methods of the present invention.

Other embodiments of the implant may be used. For example, if subconjunctval filtration is required, the drill can be used to make an opening that extends subconjunctivally. The stop that was previously on the drill would be removed. Depending on the design of the implant a small pocket could still be created in the sclera. It may not necessarily be the same size as previously described but only enough to hold the implant in position. For example, the implant may be a tube with a swelling on one or both sides, the tube may then extend further to the subconjunctival space. This type of implant would be folded in an appropriate folder and then injected into the scleral passage made by the drill. When the device returns to its normal size and shape the swellings (or other types of design) would then catch in the pocket on either side or on side of the drilled hole. This would then prevent the device from subluxating. The length of the device could also be adjusted from these fixation sites so that the tube did not protrude into the anterior chamber.

The ability to deform the intraocular pressure relieving device, and the ability of the device to return to its original, pre-deformation shape and configuration, offers a distinct advantage in that the device can be inserted through a small incision in the cornea but can be anchored to the sclera without contacting the corneal endothelium 30.

The distinct advantage of the device implanted in this manner is that there is no incision in the conjunctiva or tenons tissue. The drill approaches these tissues from underneath, ie, through the sclera. This would be visualized directly with the operating microscope. As the drill begins to penetrate, a viscoelastic substance could be then injected through the drilled passageway and move these tissues away from the sclera. The drilling could then be completed and the device inserted.

Some implants use a subconjuntival reservoir to increase the success of subconjunctival filtration. Embodiments using reservoirs could also be folded and inserted with fixation achieved through the manner described above. Again, it would be expected that the success rates of subconjunctival filtration surgery (as opposed to scleral filtration surgery) would be improved by not inciting the healing response of the conjunctiva and tenons tissue. This is accomplished by performing the surgery from inside out, using the intracameral (inside the anterior chamber) approach and not the conjunctival approach. The traditional approach is to make an incision through the conjunctiva and tenons tissue to obtain access to the anterior chamber. This starts the healing response leading to scarring and therefore blockage of the exit of aqueous from the eye and resulting increase in intraocular pressure. Since no incision with this new technique is made in the conjunctiva and tenon's tissue, this is avoided.

Furthermore, because the devices of the present invention are placed in an area remote from the anterior chamber, they are not in contact with the cells of the corneal endothelium, and thus no corneal decompensation occurs.

I claim:

1. A method of relieving intraocular pressure in an eye, the eye comprising at least an anterior chamber, a cornea, conjunctiva, tenons tissue, vascular tissue and sclera; the method comprising inserting a glaucoma drainage device into the sclera such that scleral tissue is in contact with the drainage device, and placing the glaucoma drainage device to provide fluid communication between the anterior chamber and the sclera without making an incision in the conjunctiva or tenons tissue.

* * * * *